United States Patent [19]

Boone

[11] Patent Number: 4,765,182

[45] Date of Patent: Aug. 23, 1988

[54] SYSTEM AND METHOD FOR HYDROCARBON RESERVE EVALUATION

[75] Inventor: Daniel E. Boone, Houston, Tex.

[73] Assignee: IDL, Inc., Houston, Tex.

[21] Appl. No.: 818,024

[22] Filed: Jan. 13, 1986

[51] Int. Cl.$^4$ .............................................. E21B 49/08
[52] U.S. Cl. ........................................ 73/153; 175/50; 436/30; 436/32
[58] Field of Search ................. 73/153, 151, 155; 175/48, 50; 436/28, 29, 30, 31, 32

[56] References Cited

U.S. PATENT DOCUMENTS

| | | | |
|---|---|---|---|
| 2,214,674 | 9/1940 | Hayward | 175/48 X |
| 2,328,555 | 9/1943 | Hoover, Jr. | 73/153 |
| 2,342,273 | 2/1944 | Hayward | 73/51 |
| 2,346,203 | 4/1944 | Zaikowsky | 73/51 |
| 2,694,923 | 11/1954 | Carpenter | 73/153 X |
| 2,714,308 | 8/1955 | Heck | 73/153 |
| 2,749,748 | 6/1956 | Slobod et al. | 23/153 |
| 2,883,856 | 4/1959 | Youngman | 73/23 |
| 2,938,117 | 5/1960 | Schmidt | 436/32 X |
| 3,031,571 | 4/1962 | Fearon | 250/52 |
| 3,386,286 | 6/1968 | Moore | 73/153 |
| 3,462,761 | 8/1969 | Horeth et al. | 346/1 |
| 3,495,438 | 2/1970 | Mangum | 73/19 |
| 3,512,164 | 5/1970 | Bynum | 346/1 |
| 4,286,461 | 9/1981 | Bres et al. | 73/155 |
| 4,298,572 | 11/1981 | Moffet et al. | 422/68 |
| 4,319,482 | 3/1982 | Bunner | 73/153 |
| 4,342,222 | 8/1982 | Alekhin et al. | 73/153 |
| 4,347,736 | 9/1982 | Mamadzhanov et al. | 73/155 |
| 4,536,713 | 8/1985 | Davis et al. | 324/324 |
| 4,546,640 | 10/1985 | Stone et al. | 73/19 |
| 4,635,735 | 1/1987 | Crownover | 73/155 X |

Primary Examiner—Stewart J. Levy
Assistant Examiner—Kevin D. O'Shea
Attorney, Agent, or Firm—Robert M. Carwell; Darryl M. Springs

[57] ABSTRACT

During oil and gas well drilling operations, drilling fluid volume circulated per preselected vertical borehole increment drilled is continuously measured as well as the percentage by volume of hydrocarbon gas present in the return fluid. The gas is periodically sampled and analyzed to derive a relative ratio of $C_1$ and $C_2$ present therein. A functional relationship is then periodically computed relating the drilling fluid volume circulated per vertical increment drilled, and percentage of hydrocarbon gas therein, the rock volume of cuttings from which the gas evolved, and borehole pressure and temperature conditions at which each mud sample received respective cuttings to provide a percentage gas saturation parameter per vertical foot of reservoir. In functional response to the $C_1/C_2$ ratio magnitudes, a product is derived comprised of the gas saturation value and a scaling factor yielding MCF gas/acre-foot at borehole pressure and temperature or Bbl of oil/acre-foot, yielding a direct measurement of reserves in place.

26 Claims, 2 Drawing Sheets

SYSTEM AND METHOD FOR HYDROCARBON RESERVE EVALUATION

FIELD OF THE INVENTION

This invention relates to systems and methods for deriving measurements relating to subsurface earth formations during oil and gas well drilling operations and, more particularly, relates to such systems and methods for evaluating hydrocarbon reserves from data derived during the drilling operation.

BACKGROUND OF THE INVENTION

In the search for hydrocarbon bearing subsurface earth formations, various systems and methods have been devised for providing both qualitative information regarding the presence of such formations as well as quantitative information. It has been conventional to provide for a more qualitative analysis of various characteristics of hydrocarbon-bearing formation zones by various techniques, and then to follow up subsequently with other techniques conventionally thought to be more appropriate for quantitative analysis.

For example, it has long been known that valuable information can be obtained from actual sidewall core samples of formations at borehole depths of interest which may thence be analyzed for the presence of hydrocarbons. Although such techniques have frequently been relied upon in the past primarily for their qualitative nature, several problems have nevertheless diminished their value. First, core analysts frequently see such core samples long after gas has expanded out of the sample at the surface and been dissipated in the mud and after other fluids of the sample have been otherwise lost. Other samples may have been flushed in the formation. Such techniques suffer from yet a further debility in that core recoveries may average only 30-80% of footage cored, with most of the porous rock often being lost.

Yet another technique which has often been relied upon in like manner to coring primarily for the qualitative nature of the information provided is an operation well known in the art known variously as logging while drilling or measurement while drilling. In like manner to coring, the technique also sought to directly measure and detect presence of hydrocarbons by analysis of return drilling fluids during the drilling operation. Such techniques operated on the principle that as the drilling fluid circulated, it carried along cuttings suspended therein and derived from the formation through which it circulated. More particularly, it was fundamentally assumed that the hydrocarbons in the drilling fluids evolved from cuttings suspended therein which were picked up by the fluid while adjacent the drill bit. By measuring volume of hydrocarbons per sample volume of mud returned at the surface and correlating this to formation depth when the sample was adjacent the bit, a qualitative indication of the presence of hydrocarbons as a function of borehole depth was thus obtained.

As aforesaid, once the drilling operation was halted and core samples and/or logging while drilling or "mud logging" operations completed, it was conventional to thence run a log or suite of open hole well logs or "wireline" operations such as electric logs or the like well known in the art. The purpose of such measurements was to obtain more qualitative indications of parameters from which more detailed information about the hydrocarbon bearing potential of formations at various borehole elevations could be calculated. Such logging operations basically comprised the suspension of a logging instrument from a cable which was thence lowered into the borehole while various measurements were made as a function of depth. Such measurements might include the borehole diameter by means of a caliper, electrical potential between formation beds, radioactive impurities in the formation, electrical resistivity and conductivity of the wellbore, and the like. From these measured parameters, the desired formation information could be inferred.

Unfortunately, numerous problems associated with these logging techniques have continued to plague the industry. This is so notwithstanding the seeming inherent reliability due to the measurements being made in situ at the borehole elevations of interest rather than at the remote location of the well site surface (as in the case of the previously described coring and mud logging). However, such problems arise from the fact that the presence of hydrocarbons must be inferred from these wireline parameters unlike the case of mud logs and core samples wherein hydrocarbons are detected directly from the samples. Wireline measurements rely on measurements made out into the formation through the drilling fluid-filled borehole. Accordingly, such measurements may be inherently adversely affected to varying degrees by the mud filtrate itself in terms of thickness, salinity, etc., as well as borehole irregularities, inadequate pad contact, cycle skips of acoustic logs at fractures and the like. When borehole diameters vary, the mud cake thickness may vary contributing to the unreliability of these measured parameters. Numerous attempts have been made to compensate for these borehole effects as, for example, by measuring the borehole diameter (and presumably the mud thickness) with the caliper carried on the logging string. However, several difficulties are frequently encountered nevertheless. For example, in the case of borehole wall irregularities, formation fractures, and the like, the caliper may not be providing accurate measurements of mud filtrate thickness and borehole diameter as the filtrate may have invaded the formation to a substantial degree or the caliper may have suffered from radical excursions through the fractures. Moreover, such invasion may flush hydrocarbons away from the borehole, rendering the more remote detection thereof even more difficult.

Yet an additional serious problem with wireline measurements relates to associated borehole temperature and pressure effects. A surface volume of one cubic foot of hydrocarbon gas for example, when compressed at subsurface borehole elevations resulting in 11,000 psi borehole pressure may be compressed to as little as 1/550 of its original volume, or 0.0018 cubic feet, rendering it difficult to detect such minute gas particles in subsurface environments.

With the aforementioned limitations of subsurface logging in mind and returning now to a further discussion of the logging while drilling technique, one such operation may be seen disclosed in U.S. Pat. No. 2,328,555 entitled "Well Logging Method" to Herbert Hoover, Jr. This system illustrates some inherent deficiencies which have been overcome by the present invention. It will be recalled that in prior logging while drilling operations, they were employed often primarily for their qualitative indicators of potential hydrocarbon bearing formations or "shows" which were later quantitatively confirmed by other techniques such as wireline.

Accordingly, such systems typically only calculated percentages of hydrocarbon gas per volume of return drilling fluid with no attempts to employ such measurements for quantitative formation reserves evaluation on a regular and continuous basis while drilling as, for example, in a volumetric analysis of hydrocarbon reserves per vertical foot drilled. Such prior art systems were content, as in the hereinbefore noted Hoover system, with a "batch" process analysis. In this system, a sample of drilling fluid was simply periodically withdrawn from the mud system and analyzed by a conventional gas chromatograph technique for relative presence of light and heavy hydrocarbons, or the like. The data was thence related to depth when the mud sample was adjacent the drill bit. Operators would, in fact, from time to time, calculate reserves from logging while drilling data for example by estimating average porosity values over formation intervals of interest wherein gross bed thicknesses of sand, for example, were simply "eyeballed". However, the prior art overlooked the possibility of obtaining direct downhole formation hydrocarbon reserve volumes on a regular basis per incremental borehole depth.

These and other deficiencies of the prior art have been overcome by the systems and methods of the present invention which will be described hereinafter in greater detail with reference to the accompanying drawings.

SUMMARY OF THE INVENTION

A system and method for identifying hydrocarbon productive zones providing direct measurement of oil and gas reserves in place.

The volume of drilling fluid circulated in an ongoing drilling operation is measured at the wellsite surface per a preselected vertical increment of formation drilled. The volume of total hydrocarbon gas in the drilling fluid volume is also periodically monitored at the surface, from which a percentage hydrocarbon gas by volume in the drilling fluid may be determined. From the known drillbit diameter and the drilling rate, the volume of formation drilled per the preselected vertical borehole increment and circulated drilling fluid volume is determined. The percentage gas in drilling fluid parameter is then correlated to this volume of formation drilled to yield a percentage gas per unit of volume of formation drilled or percentage gas saturation as a function of borehole depth. These values are corrected from wellsite surface conditions to borehole pressure and temperature conditions at the borehole elevations corresponding to the depth at which the formation volumes were drilled. A function is accordingly derived corresponding to gas saturation per unit of formation drilled corrected to borehole pressure and temperature conditions at successive borehole elevations.

For each volume of drilling fluid corresponding to a particular drilled formation volume, light and heavy hydrocarbon volume therein are detected and a ratio of $C_1/C_2$ derived. For values of $C_1/C_2$ within first and second ranges of 2-6 or 6-50 for example, oil or gas is assumed to be present at that borehole increment, respectively. Accordingly, at each borehole interval for which a gas saturation value has been determined, that gas saturation value may be multiplied by a constant dependent upon which range the $C_1/C_2$ ratio for that borehole interval falls within to arrive at a direct volumetric indication of hydrocarbon reserves in terms of Bbl/acre-feet or MCF/acre-feet at that interval, whether it be oil or gas. These constants are 7758.34 and 43.56 and correspond to conversion factors for converting Bbl and MCF to conventional acre-feet, respectively. By adding up such volumetric hydrocarbon reserve indications at successive borehole elevational increments, an indication of volumetric oil or gas hydrocarbon reserves may be obtained for any desired vertical increment of borehole formation.

DETAILED DESCRIPTION OF THE INVENTION

Figure 1:
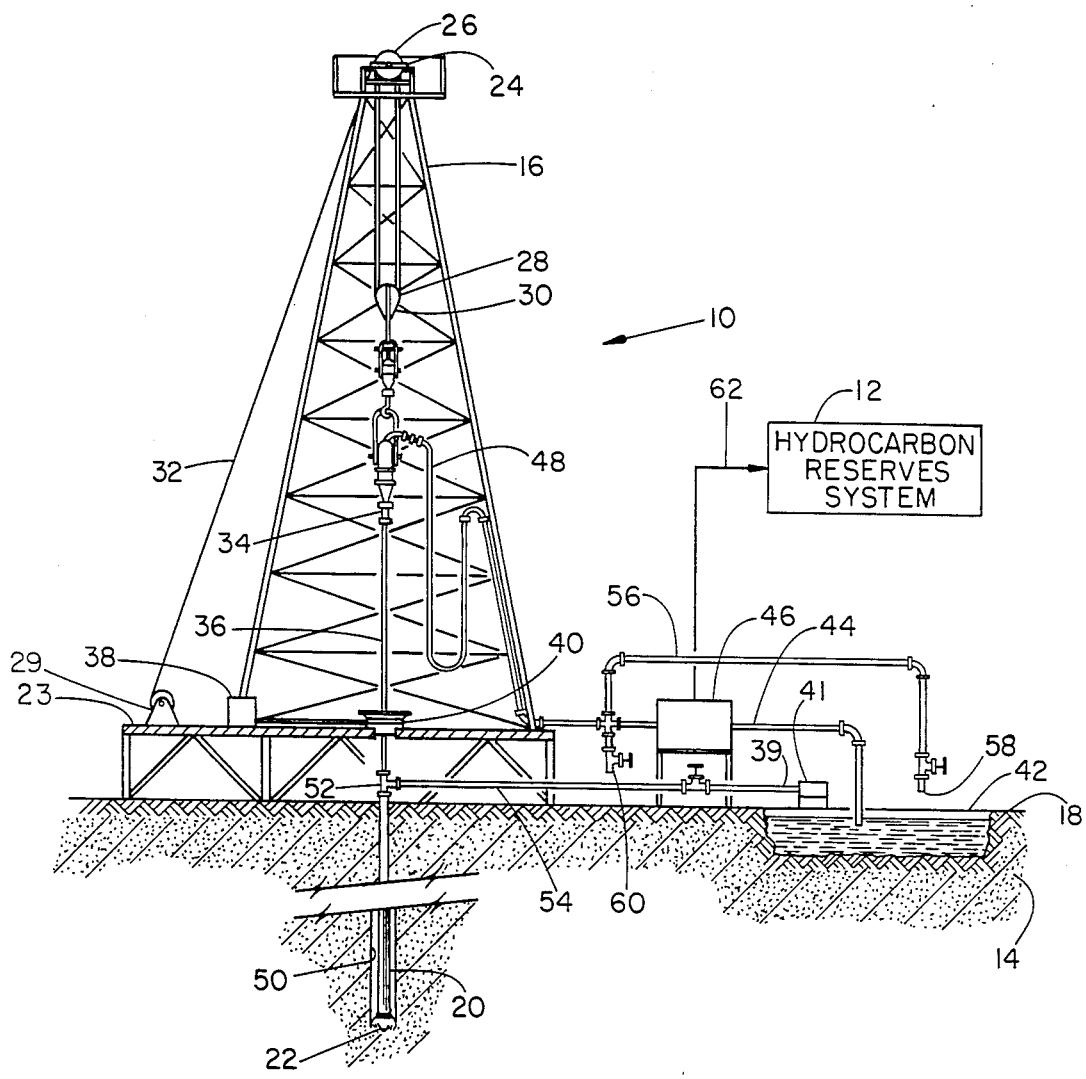
FIG. 1 is an illustration, partly schematic and partly in section, depicting a typical surface oil and gas well drilling equipment system to which the invention is applicable.

With reference to FIG. 1, a rotary drilling system 10 will be seen generally depicted therein for drilling oil and gas wells in subsurface earth formations 14. A derrick 16 is provided which rests upon the earth surface 18 for purposes of supporting, raising, lowering, and rotating a drill pipe string 20 during drilling operations as well as for delivery and rotation of other tubular goods and devices in the borehole.

Disposed at the distal end of drill string pipe 20 is a rotary drill bit 22 for penetrating the formation 14 upon rotation thereof as hereinafter described. At the uppermost portion of derrick 16, a crown block 24 may be seen carrying a pulley 26. A motor 38 resting on platform 23 has extending therefrom a drilling cable 32 which traverses a pulley 29. From the pulley 29, the cable 32 extends over the pulley 26 and thence is repeatedly routed between pulley 26 and a pulley 28 carried by traveling block 30 which is pendantly disposed from the cable 32.

A swivel 34 hangs from the block 30 having attached thereto a kelly 36 for purposes of imparting a rotary motion to the drill string 20 in a manner well known in the art. In operation, the purpose of the cable 32, motor 38, pulleys 26, 28, and 29, and blocks 24 and 30 are primarily to provide for vertical upwards and downwards movement of the drill string 20 so as to permit connection and disconnection of drill pipe sections to the string 20 as desired.

Still referring to FIG. 1, a rotary table 40 is provided in platform 23 for imparting rotary motion to the drill string 20 during the drilling operation. A sump 42 adjacent the platform contains drilling fluid entering and exiting from the borehole. An inlet pipe 44 is further included for withdrawing drilling fluid from the sump 42 and delivering it to a suitable mud pump 46. A hose 48, in turn, receives the mud pumped from the pump 46 and delivers it through the swivel 34 kelly 36, rotary table 40, and bell nipple 52 into the annulus defined by the drill pipe 20.

In the conventional manner, mud from the sump 42 thus delivered into the interstices of the drill pipe 20 will circulate downwards therethrough and about the bit 22 thereby lubricating it and carrying away cuttings from the formation 14. The circulating drilling fluid will thence, as a result of the pumping operation, travel upwards between the outer wall surface of the drill pipe 20 and the borehole wall 50 until it reaches the aforementioned drill collar. At the nipple 52, it will be noted that a discharge pipe 54 will be provided for receiving this upwardly moving drilling fluid which contains the cuttings made by the bit 22. The drilling mud will thence be discharged out the end of outlet pipe 39 through a screen 41 and back into the sump 42. A bleeder line 56 may further be provided which may selectively route mud from the sump 42 through the pump 46 and back to the sump 42, discharging at the end 58 of the bleeder line 56. Additionally, a mud faucet 60 may be provided interconnected to the hose 48, again, for selectively withdrawing mud from the pump 46 as desired. It will be appreciated that the hereinbefore described general drilling system has been greatly simplified inasmuch as numerous components and variations well known in the art have been omitted. For example, it is conventional in the art to provide for delivery of return mud from the discharge pipe 54 into a "possum belly" tank (not shown), the overflow thereof being delivered into a shale shaker for purposes of reducing the cuttings content of the return mud prior to its return to the sump 42. In like manner, it is further conventional to provide for degaser equipment whereby when the mud becomes excessively gas cut thereby reducing its effective weight and ability to provide a sufficient hydrostatic head for prevention of blowouts and the like, the degaser will draw a vacuum on the return mud so as to draw the undesirable gas carried therein out of the mud. Accordingly, it will be appreciated that the invention is not intended to be limited to any one particular drilling operation system and admits of numerous variations thereof as being within the scope of the present invention.

Still referring to FIG. 1, there will further be seen depicted therein a schematic block diagram captioned hydrocarbon reserve system 12 which will be hereinafter described in greater detail. The system 12 is shown as being functionally interconnected to the rotary drilling system 10 by means of data line 62. Whereas, in the figure, this line 62 is shown as originating from the pump 46, it is merely intended to schematically indicate that various parameters and measurements to be hereinafter described may be derived from the various components of the drilling system 10 and electronically delivered on the line 62 to the system 12 for purposes to be hereinafter described. For example, as will be discussed in greater detail hereinafter, data relating to the volume of mud being pumped by the pumper 46 as well as chemical and volumetric analysis of the gas contained within the mud in the sump 42 will be desired. This line 62 is thus intended to indicate delivery of the necessary data to the system 12 for derivation of such parameters and mathematical and electronic operation thereon as hereinafter described.

Now that the overall system has been described, a general description of the theory and principles of the present invention will be given. This will be followed by a detailed description of the hydrocarbon reservoir system 12 of FIG. 1 depicted in greater detail and FIG. 2, whereby the purposes of the system and components thereof will thus be made more clear. In accordance with the present invention, during drilling operations, it is first desirable to derive periodically a measurement of the volume of drilling fluid being circulated through the drill string 20 per vertical linear foot of formation drilled. This may be done by means of an electrical signal from the pump 46. More particularly, by knowing the number of strokes of the pump per linear foot drilled, and the pump capacity in terms of mud volume pumped per stroke, the desired mud volume per linear drilled foot may be obtained.

Next, it is desirable to derive measurement of the percentage of hydrocarbon gas by volume present at the surface and at atmospheric pressure conditions at surface temperatures in each such measured volume of drilling fluid per linear foot drilled and being returned to the sump 42. Various techniques well known in the art for accomplishing this are available, such as the familar "hot-wire" method. In this technique, mud from the discharge pipe 54 is routed through a mud trough or possum belly (not shown) primarily to catch drill cuttings. A gas extractor in the mud trough at the end of the flow line 54 agitates mud with a stirring device to release gas entrained in the mud. The gas is routed to a hot-wire gas detector which detects gas volume per volume of mud. An appropriate computer or signal processor may then interrogate the gas detector periodically (such as at 5 second intervals) to derive a periodic average measurement of volumetric percentage of gas in the mud, as for example, such an average being derived per linear foot drilled.

With the volume of drilling fluid circulated per linear foot drilled being known and the percentage gas (by volume) entrained in the mud (averaged over periodic time intervals), it is further necessary to determine the volume of formation drilled through for the given vertical foot of formation. This volume per linear foot drilled is assumed to be a constant cylindrical volume and, accordingly, varies as the square of the diameter of the bit.

It may also be periodically made available in an appropriate signal processor and at appropriate preselected depth intervals. For example, formation volume drilled for each vertical foot may be derived by any convenient means employing a periodic depth interrupt signal and depth data produced by a depth system or other mechanism at preselected increments of borehole depth.

It is assumed that the gas which evolved and was measured from the volume of mud which circulated per linear foot drilled came from the rock volume of formation drilled through, inasmuch as the cuttings from the formation volume will be suspended in the volume of mud. Accordingly, it will be appreciated that by multiplying the percentage gas in the mud volume per foot drilled by the mud volume circulated per linear foot drilled, the result will be the gas volume entrained in the mud. Moreover, by dividing this gas volume in the mud by the volume of formation drilled per linear foot, the gas saturation or percentage of gas in the volume of formation per foot drilled will be given.

It will be appreciated that the aforementioned percentage gas saturation is at surface conditions of pressure and temperature, inasmuch as the hydrocarbon gas is detected at the surface. However, hydrocarbon reserves are typically defined at borehole conditions. Thus, it may be desirable to convert this gas saturation percentage to an equivalent corresponding to the borehole depth at which the cuttings become entrained in the mud volume under consideration. This may be accomplished by borehole pressure and temperature gradient conversion factors well known in the art, resulting in percentage of hydrocarbon volume at borehole pressures and temperature conditions attributable to the rock volume.

The apparatus of the present invention will further desirably be provided with means for periodically detecting the ratio of light to heavy hydrocarbons, thus providing an output proportional to $C_1/C_2$, where $C_1$=methane gas and $C_2$=ethane gas. It is generally accepted in the art that such a ratio within a range of 2–6 corresponds to an oil and wherein a range of 6–50 corresponds to a gas. Such apparatus may conveniently take the form of a gas chromatograph which samples gas from the preselected mud volume and analyzes it quantitatively in a well known manner to derive measurements of $C_1$, $C_2$, $C_3$, and $C_4$ present in the mud.

Accordingly, for the volume of mud and formation under consideration, a multiplier conversion factor is selected as a function of the ratio determined for the mud and formation volume in question. More particularly, if the ratio is 2–6, a conversion factor of 7758.34 is selected corresponding to a Bbl/acre-foot familiar to the art. Conversely, if the ratio is found to be between 6–50, the conversion factor of 43.56 is selected corresponding to MCF/acre-foot at borehole temperatures.

It will thus be appreciated that by multiplying the previously described gas saturation values by the particular conversion factor in functional relation to the ratio just described, a volumetric indication in terms of volume of either oil or gas in Bbl/acre-feet or MCF/acre-feet is thereby provided for the preselected linear borehole foot.

Moreover, it will further be appreciated that the hereinabove described process may be repeated for successive one foot increments of borehole or at any other increments. This may be done by deriving, for successive such increments, corresponding measurements of formation volume per linear foot drilled, drilling fluid volume circulated per linear foot drilled, and gas volume per such drilling fluid volume. By combining these parameters in the manner just described, translating the result to borehole temperature and pressure conditions, and applying the appropriate conversion factor (dependent upon the $C_1/C_2$ ratio determined for the gas in the mud over the interval), the volume indication of hydrocarbon reserves in place at borehole pressure and temperature conditions in the next increment of borehole may be arrived at. Still further, by totalling such values corresponding to adjacent increments of borehole, total potential hydrocarbon reserves in place for a show or formation bed of any width desired may be readily determined at downhole conditions. The mathematical functional relationships hereinabove described are as follows:

Equation 1:
$$\% \text{ GAS SATURATION} = \frac{(\% \text{ Gas})(\text{Bbl Mud})(5.6146)(14.65)(460 + BHT)}{(14.65 + BHP)(460 + 100)} \times \frac{1}{(.00545 D^2)}$$

Where
% GAS SATURATION or "% GASAT"=Volume of hydrocarbons in a cylindrical formation volume one foot high with a diameter "D" at BHT and BHP conditions, in percent
D=Bit diameter in inches
% Gas=Hydrocarbon gas volume per unit volume of circulated drilling fluid at surface conditions, in percent
BHT=Bottomhole temperature in °F. at borehole elevation where formation volume originated (measured or calculated from borehole elevation)
BHP=Bottomhole pressure in psi at borehole elevation where formation volume originated (measured or calculated from borehole elevation)
Bbl=Volume of drilling fluid circulated downhole per vertical borehole foot drilled FOR GAS ($6 < C_1/C_2 < 50$)    Equation 2:
$$\text{VOLUME (in MCF/Acre-Foot)} = \% \text{ GAS SATURATION} \times \frac{1}{100} \times 43.56$$

FOR OIL ($2 < C_1/C_2 < 6$)    Equation 3:
$$\text{VOLUME (in Bbl/Acre-Foot)} = \% \text{ GAS SATURATION} \times \frac{1}{100} \times 7758.34$$

Where
43.56 and 7758.34 are conversion factors for converting a unit volume of formation to MCF/acre-foot or Bbl/acre-foot, respectively.

Figure 2:
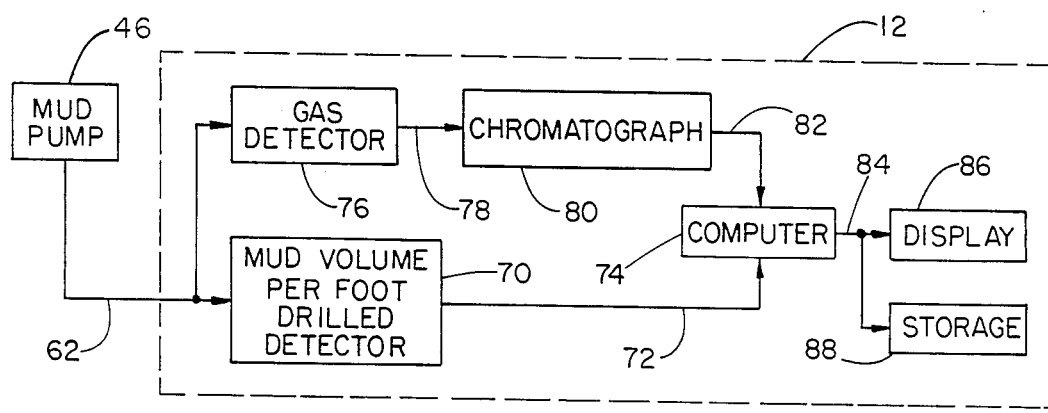
FIG. 2 is a schematic diagram indicating in greater detail the components comprising the hydrocarbon reserves system depicted in FIG. 1.

Now that a generalized theoretical discussion of the principles of the present invention has been given, the purposes of the components depicted in FIG. 2 may be more readily understood. Accordingly, with reference to FIG. 2, the hydrocarbon reserves system 12 of FIG. 1 will be seen depicted therein in greater detail. From the foregoing, it will be recalled that it is desirable to periodically obtain measurements of the drilling fluid volume per linear foot drilled. Accordingly, the module indicated by reference number 70 is intended functionally to perform this function as a component part of the system 12. As aforesaid, this may be done by means of any convenient electrical system. It will be recalled that in one such convenient system as previously described, the module 70 may receive on the signal line 62 from the drilling system 10 parameters such as depth interrupts indicating the successive passage of the drill bit 22 through preselected borehole increments. Also carried on line 62 may be constants preset in the module 70 indicating the incremental Bbl per stroke of the mud pump 46, as well as signals indicating the number of such strokes which have transpired between successive such depth interrupts. From such parameters, the mud volume detector 70 may generate an electrical signal output on line 72 indicating the volume of mud or drilling fluid circulated through the drill string 20 per preselected increment of linear borehole depth drilled such as on a per foot basis, with such data being delivered on line 72 to an appropriate computer 74.

It will further be recalled that in accordance with the teachings of the present invention, it is desirable to derive for the aforementioned mud volume detected by the module 70 a volume of entrained gas within such mud volume. Accordingly, the line 62 being delivered to the gas detector 76 of the system 12 is further intended to schematically depict that, as previously described with respect to the mud trough, the gas detector may be any convenient such detector well known in the art for deriving such a measurement. More particularly, in one embodiment, means will be provided in the mud trough for agitating the mud and collecting samples thereof which are volumetrically measured by the gas detector 76 for example on a time basis increment of 5 seconds or the like. An electrical signal indicated by line 78 is thence delivered by the gas detector 76 to the computer 74 (shown for convenience as being delivered through the chromatograph 80 and thence on line 82 to the computer 74). The gas detector 76 may also receive depth interrupts on line 62 in like manner to those delivered to the mud volume detector 70, such depth interrupts being generated by the computer 74 in response to depth pulses from the sheave wheel of the drilling system 10. Upon receipt of such depth interrupts, the gas detector 76 will deliver to the computer 74 the currentmost 5 second integrated gas volume. The computer 74 may thence relate this last value of the gas volume to the last value for mud volume per foot drilled delivered to the detector 70. The computer 74 may thence calculate a gas volume detected per mud volume measured for a given borehole increment such as one foot, so as to derive a percentage of gas entrained in the mud at the surface.

Also, with the foregoing theoretical discussion in mind, it will be noted from FIG. 2 that a chromatograph 80 is provided. In response to gas samples delivered on the line 78 from the gas detector 76, the chromatogragh 80 will periodically continue to recalculate light to heavy hydrocarbon ratios $C_1/C_2$ in the aforementioned manner. Again, in response to appropriate depth interrupts from the computer 74, the chromatograph module 80 may deliver on line 82 digital signals to the computer 74 corresponding to the latest time average of such a ratio or the value for such a ratio corresponding to gas detected in a mud volume circulated per foot drilled as indicated from the module 70.

Figure 3:
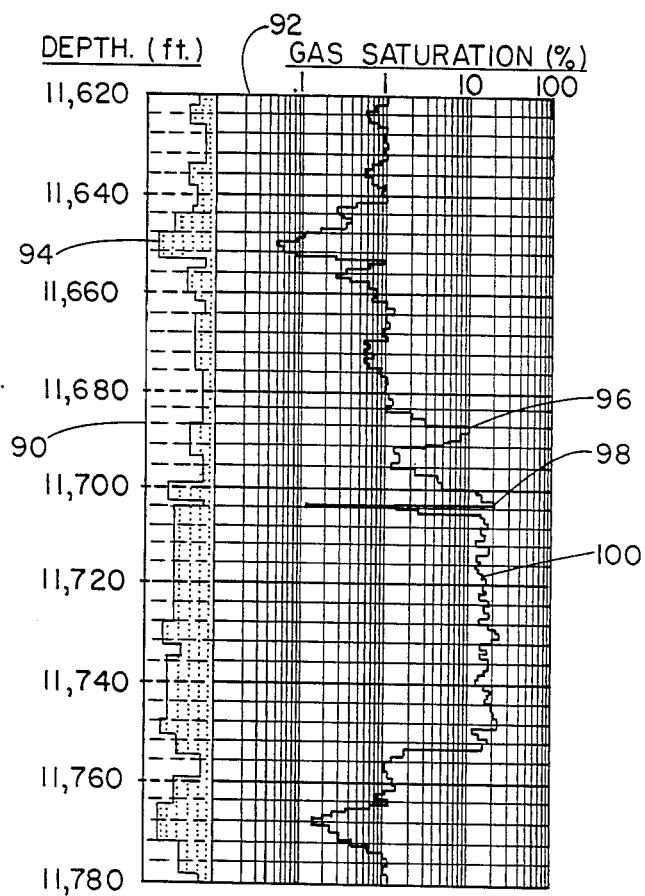
FIG. 3 is a representative well log obtained in accordance with the practice of the invention.

Additionally stored in the computer 74 will be the previously described conversion factors well known in the art for converting surface pressure and temperatures to borehole conditions as well as the conversion factors for converting gas saturations to MCF/acre-feet and the Bbl/acre-feet. Also contained in the computer 74 will be routines for calculating the $C_1/C_2$ ratios, and further subroutines for calculating the desired hydrocarbon reserves at each desired borehole increment in functional response to the hereinaboved noted functional relationships. As aforesaid, depth interrupt information being delivered to the computer 74 will enable the computer to correlate the various measurements for mud volume per foot drilled, gas volume in the mud volume per foot drilled, and chromatograph detection signals so as to ensure that proper values are functionally multiplied together corresponding to th appropriate parameter data derived at corresponding borehole depths. Finally, with reference to FIG. 2, it will be noted that the computer 74 is schematically depicted as having an output 84 delivered to an appropriate display device 86 and storage 88. It may be desirable for the hydrocarbon reserve volumetric data to be displayed in some convenient form, as for example, in the manner of a logarithmic strip chart well known in the art wherein such values are successively displayed corresponding to successive increments of borehole depth. Similarily, it may be desirable simply to store computer digital values carried by line 84 in appropriate digital storage 88 for subsequent processing. It will be appreciated that the format and content of information shown in display 86 and stored in the storage 88 may vary widely in accordance with the desired format and informational content and the like. Accordingly, the invention is not intended to be so limited to any particular display or sets of data stored. For example, in some applications it may be desirable to print out in real time a logging curve corresponding to actual hydrocarbon reserve volumes as a function of borehole depth. However, in other such applications, it may be sufficient merely to provide, as indicated in FIG. 3, a logging curve corresponding simply to the percentage of gas saturation, i.e., the percentage of hydrocarbon volumetrically per volume of formation. Upon subsequent analysis of the analysis and interpretation of the log, these gas saturation values at subsequent borehole depths may be manually multiplied by the appropriate conversion factor (either MCF/acre-feet or Bbl/acre-feet) corresponding to the $C_1/C_2$ ratios and other analytical factors in order to determine actual hydrocarbon reserve volumes.

With reference now to FIG. 3, there will be seen depicted therein, an illustration of the present invention showing logging data derived from an actual oil and gas well located in southern Louisiana. First, it will be noted from reference numeral 90 that the ordinate indicates borehole depth in feet and, for the segment of the log therein depicted, the borehole increment of interest ranges from 11,620 to 11,780 feet.

Still referring to FIG. 3, with respect to the abscissa 92, it will be recognized as a conventional logarithmic scale wherein the previously described gas saturation parameter in percent is indicated. Also included in the log of FIG. 3 is a lithology curve 94 derived from porosity data and the like wherein the dotted segments indicate relative proportion of sand. Superimposed on the logarithmic portion of the log of FIG. 3 will be seen the actual log trace 96 corresponding to the gas saturation values described herein. It will be noted from the log that three zones of interest have been identified by reference numerals 96, 98, and 100 referring, respectively, to interval A at depth 11,698–11,691, interval B at depth 11,698–11,702, and interval C corresponding to the depth interval 11,705–11,753.

With reference to the accompanying table, the aforementioned intervals A–C may be seen to have listed associated therewith percentage gas saturation values (at bottomhole conditions) calculated in accordance with the method described herein from values of mud volume per foot drilled, gas volume per mud volume (i.e., percentage gas in mud), the $C_1/C_2$ ratios and the like (not shown). In the column captioned "Reserves in Interval of Interest" numbers will be seen listed therein corresponding to surface reserves calculated for each appropriate depth interval in accordance with the hereinbefore noted functional relations defined in the equations previously described. A representative example of derivation of a calculated reserve listed in Table 1 for the borehole depth of 11,701 feet will follow hereinafter for clarity:

TABLE 1

| DEPTH | POROSITY | % GASAT | PORSAT | SW | SURFACE RESERVES VOLUME AT STANDARD PRESSURE (14.65 psi) & STANDARD TEMPERATURE (65° F.) | RESERVES IN INTERVAL OF INTEREST |
|---|---|---|---|---|---|---|
| 11687 | 10 | 3.0 | 30 | 70 | | |
| 88 | 10 | 3.0 | 30 | 70 | | |

TABLE 1-continued

| DEPTH | POROSITY | % GASAT | PORSAT | SW | SURFACE RESERVES VOLUME AT STANDARD PRESSURE (14.65 psi) & STANDARD TEMPERATURE (65° F.) | RESERVES IN INTERVAL OF INTEREST |
|---|---|---|---|---|---|---|
| 89 | 17 | 10.2 | 60 | 40 | 1878: | Interval A (96) |
| 90 | 16 | 8.8 | 55 | 45 | 1620:3' | 4566 MCF/ |
| 91 | 13 | 5.9 | 45 | 55 | 1068: | Acre-Foot |
| 92 | 10 | 3.0 | 30 | 70 | | |
| 93 | 9 | 1.3 | 14 | 86 | | |
| 94 | 11 | 1.5 | 14 | 86 | | |
| 95 | 11 | 1.5 | 14 | 86 | 276 | |
| 96 | 9 | 1.3 | 14 | 86 | 239 | |
| 97 | 11 | 2.2 | 20 | 80 | 405 | |
| 98 | 14 | 4.5 | 32 | 68 | 828: | Interval B (98) |
| 99 | 15 | 4.5 | 32 | 68 | 828: | 11506 MCF/ |
| 11700 | 20 | 14.0 | 70 | 30 | 2578:5' | Acre-Foot |
| 1 | 25 | 17.5 | 70 | 30 | 3222: | |
| 2 | 31 | 22.0 | 72 | 28 | 4050: | |
| 3 | 3 | 0.4 | 14 | 86 | 74 | |
| 4 | 10 | 1.4 | 14 | 86 | 258 | |
| 5 | 13 | 2.6 | 20 | 80 | 479: | Interval C (100) |
| 6 | 20 | 13.0 | 65 | 35 | 2394: | 145,841 MCF/ |
| 7 | 22 | 15.0 | 67 | 33 | 2762: | Acre-Foot |
| 8 | 25 | 17.5 | 70 | 30 | 3222: | |
| 9 | 23 | 15.0 | 65 | 35 | 2762: | |
| 10 | 24 | 16.0 | 67 | 33 | 2946: | |
| 11 | 24 | 17.0 | 71 | 29 | 3130: | |
| 12 | 21 | 14.0 | 67 | 33 | 2578: | |
| 13 | 26 | 19.0 | 73 | 27 | 3498: | |
| 11714 | 26 | 18.0 | 69 | 31 | 3314: | |
| 15 | 22 | 14.0 | 64 | 36 | 2578: | |
| 16 | 22 | 15.0 | 68 | 32 | 2762: | |
| 17 | 20 | 13.0 | 65 | 35 | 2394: | |
| 18 | 21 | 14.0 | 67 | 33 | 2578: | |
| 19 | 23 | 16.0 | 69 | 31 | 2946: | |
| 20 | 24 | 17.0 | 71 | 29 | 3130: | |
| 21 | 24 | 16.0 | 67 | 33 | 2946: | |
| 22 | 23 | 15.0 | 65 | 35 | 2762: | |
| 23 | 23 | 15.0 | 65 | 35 | 2762: | |
| 24 | 22 | 15.0 | 68 | 32 | 2762: | |
| 25 | 26 | 18.0 | 70 | 30 | 3314: | |
| 26 | 26 | 17.0 | 65 | 35 | 3130: | |
| 27 | 25 | 18.0 | 72 | 28 | 3314: | |
| 28 | 20 | 13.0 | 64 | 36 | 2394: | |
| 29 | 26 | 18.0 | 70 | 30 | 3314: | |
| 30 | 29 | 21.0 | 72 | 28 | 3866: | |
| 31 | 31 | 22.0 | 71 | 29 | 4051: | |
| 32 | 29 | 20.0 | 69 | 31 | 3682: | |
| 33 | 23 | 15.0 | 65 | 35 | 2762: | |
| 34 | 27 | 17.0 | 63 | 37 | 3130: | |
| 35 | 25 | 15.0 | 60 | 40 | 2762: | |
| 36 | 27 | 17.0 | 63 | 37 | 3130: | |
| 37 | 28 | 19.0 | 68 | 32 | 3498: | |
| 38 | 25 | 16.0 | 64 | 36 | 2946: | |
| 39 | 23 | 15.0 | 65 | 35 | 2762:49' | |
| 40 | 21 | 13.0 | 62 | 38 | 2394: | |
| 41 | 26 | 17.0 | 65 | 35 | 3130: | |
| 42 | 27 | 18.0 | 67 | 33 | 3314: | |
| 43 | 26 | 18.0 | 69 | 31 | 3314: | |
| 44 | 24 | 17.0 | 71 | 29 | 3130: | |
| 45 | 26 | 18.0 | 69 | 31 | 3314: | |
| 46 | 27 | 18.0 | 67 | 33 | 3314: | |
| 47 | 29 | 20.0 | 69 | 31 | 3682: | |
| 11748 | 32 | 22.0 | 69 | 31 | 4050: | |
| 49 | 31 | 22.0 | 71 | 29 | 4050: | |
| 50 | 19 | 11.0 | 58 | 42 | 2025: | |
| 51 | 22 | 13.0 | 59 | 41 | 2393: | |
| 52 | 23 | 14.0 | 61 | 39 | 2578: | |
| 53 | 20 | 13.0 | 65 | 35 | 2393: | |
| 54 | 12 | 1.8 | 15 | 85 | 331 | |
| 55 | 13 | 1.3 | 10 | 90 | 239 | |
| 56 | 13 | 1.3 | 10 | 90 | 239 | |
| 57 | 15 | 1 | 7 | 93 | 184 | |
| 58 | 23 | 1.1 | 5 | 95 | 202 | |
| 59 | 20 | 1.2 | 6 | 94 | 221 | |
| 60 | 20 | 1.4 | 7 | 93 | 258 | |

| Example | |
|---|---|
| Depth | 11,701 Feet |
| Bit Size | 8.75 inches |
| % Gas in Mud (measured at surface) | 20.5% |
| Mud Volume (circulated per linear foot of formation drilled at 11,701 feet) | 28.4 Barrels |
| Bottomhole Temperature (at 11,701 feet) | 271° F. |
| Bottomhole Pressure (at 11,701 feet) | 8578 psi |
| Surface Gas Sample Temperature | 100° F. |
| Atmospheric Pressure | 14.65 psi |

From Equation 1: % GAS SATURATION =

$$\frac{(\% \text{ Gas})(\text{Bbl Mud})(5.6146)(14.65)(460 + BHT)}{(.00545\ D^2)(BHP + 14.65)(460 + 100)} =$$

$$\frac{(20.5\%)(28.4\ \text{Bbl})(5.6146)(14.65)(460 + 271)}{(8.75)^2(.00545)(8578 + 14.65)(460 + 100)} = 17.5\%$$

This value corresponds to the entry in the "% GASAT" column at 11,701 feet of Table 1.

It will be noted that in the intervals B and C, a $C_1/C_2$ ratio between 6–50 was detected indicating presence of gas and accordingly Equation 2 is employed.

It will further be noted that in Table 1 reserves are shown at surface conditions (i.e., standard temperature, pressure). Accordingly, the fact that the % GASAT measurements are at borehole conditions at 11,701 feet (Equation 2) means they must be compensated for when applied to yield surface reserves as follows:

Standard Atmospheric Pressure $(SP)$ = 14.6 psi

Standard Atmospheric Temperature $(ST)$ = 65° F.

Surface Resever Volume = Equation 2 ×

$$\frac{(BHP + SP)(460 + ST)}{(SP)(460 + BHT)}$$

$$= (17.5\%) \times \frac{1}{100} \times$$

$$\frac{43.56(8578 + 14.6)(460 + 65°)}{(14.6)(460 + 271°)}$$

= 3222 MCF/Acre-Foot

Still with reference to Table 1, it will be noted in the far right column captioned "Reserves in Interval of Interest" that the calculated reserves per foot listed for all the depth intervals of the particular interval have been summed to yield a combined total of hydrocarbon reserves for the entire borehole increment comprising the interval. It is of significant interest to note that in accordance with the present invention, the intervals A-C were determined to be of productive sands, such interpretation being borne out by sidewall cores. However, it is even further of note that conventional electric wireline logs condemned the sands in these intervals of interest as being water wet and accordingly non-productive.

Several additional aspects of the invention herein disclosed must be noted. First, it should be readily apparent that a time lag exists between location of the drill bit 22 at a particular borehole depth and when drilling fluid adjacent the bit at that depth has finally traversed up the entirety of the borehole to the well site surface wherein such mud sample may be analyzed. In other words, in real time as a mud sample is being analyzed at the surface, the characteristics thereof in terms of gas volume entrained therein and the like will correspond not to borehole elevations at which the drill bit 22 is positioned during such analysis. Rather, such analysis of a given mud sample at the surface will correspond to a shallower borehole depth at which the bit 22 and uphole sample were positioned earlier in time. Accordingly, means must be provided which are well known in the art for "lagging" the data to compensate for this time lag between current indicated depth and the prior shallower depth at which surface mud samples were located when they are undergoing current analysis at the surface. The degree of such lag compensation is obviously functionally related to the drilling rate and may be accounted for in the data by the computer 74 and in manners well known in the art.

Also, it has been found that shale lithology has the most reliable gas saturation inasmuch as it is a compacted rock of uniform structure exhibiting very little difference in pore space from one form of shale to another. Accordingly it has been found empirically that the gas saturation of shale normally falls within the area of approximately 1% gas saturation, i.e., a "shale line" well known in the art should be set to indicate approximately a 1% gas volume presence in the rock. Thus, it is conventional practice to employ multipliers on the individual data points appearing on the log, such as those of FIG. 3, in order to ensure that these data points corresponding to the shale line in fact appear substantially about the 1% gas saturation coordinate. The reason for the necessity for such compensation is well known in the art and includes such factors as the gas traps for detecting gas having defective paddles, or being set too high in the mud trough so as to draw too much air giving too low a gas reading, or the like.

Still further, it will be recalled that when the $C_1/C_2$ ratio was found to be approximately within the ranges of 6–50, and 2–6, presence substantially of gas for oil was assumed, respectively. Accordingly, corresponding Equations 2 or 3 were employed to apply the appropriate correction factor to the percentage GASAT parameter to convert to MCF/acre-feet (for gas) or Bbl/acre-feet (for oil).

However, it will be appreciated that choice of such ranges for $C_1/C_2$ ratios is to a certain extent subjective and arbitrary and the invention is accordingly not intended to be so limited. For example, reservoirs will typically be comprised of a combination of oil and gas reserves. Thus, it is contemplated by the present invention to apply appropriate conversion factors to the percentage GASAT parameter in functional relation to a characterization of the reservoir in terms of relative presence of gas and oil however determined. Moreover, it will be noted that the conversion factors employed are in terms of conventional units of hydrocarbon volume well known in the art such as MCF/acre-feet in the case of gas and Bbl/acre-feet in the case of oil, although the invention is not intended to be so limited. Accordingly, the percent GASAT parameter may be multiplied by any appropriate constant conversion factor dependent upon the characterization of the reserve in terms of relative oil and gas content to yield a volumetric reservoir hydrocarbon determination in terms of any desired unit which may, if desired for example, be metric equivalents thereof.

It is therefore apparent that the present invention is one well adapted to obtain all of the advantages and features hereinabove set forth, together with other advantages which will become obvious and apparent from a description of the apparatus itself. It will be understood that certain combinations and subcombinations are of utility and may be employed without reference to other features and subcombinations. Moreover, the foregoing disclosure and description of the invention is only illustrative and explanatory thereof, and the invention admits of various changes in the size, shape and material composition of its components, as well as in the details of the illustrated construction, without departing from the scope and spirit thereof.

What is claimed is:

1. A method of direct quantitative determination of a measure of hydrocarbon reserves present in a subsurface earth formation, while drilling a borehole therethrough with a drill bit, comprising the steps of:

measuring the vertical depth of said borehole in linear incremental units, determining the volume of the subsurface earth formation displaced by the borehole per each of said linear incremental units of depth, measuring the volume of drilling fluid circulated into the borehole during drilling per a selected linear incremental unit of depth, detecting the presence of hydrocarbon gases in a preselected unit volume of drilling fluid recovered at the earth's surface from said measured volume of drilling fluid, measuring the volume of said detected hydrocarbon gases present in said preselected unit volume of drilling fluid, determining the subsurface formation pressure and temperature associated with said selected linear incremental unit of borehole depth associated with said preselected unit volume of drilling fluid carrying said hydrocarbon gases, determining the percentage of hydrogen gas saturation for said selected linear incremental unit of borehole depth in the subsurface earth formation that is functionally related to said volume of hydrocarbon gases recovered at the earth's surface present in said preselected unit volume of drilling fluid corrected to the subsurface earth formation pressure and temperature at said selected linear incremental unit of borehole depth expressed as a percentage of said volume of the subsurface earth formation displaced by the borehole in said selected linear incremental unit of borehole depth, detecting the presence of a plurality of preselected hydrocarbon gases present in said preselected unit volume of drilling fluid recovered at the earth's surface from said measured volume of drilling fluid, measuring the volume of each of a preselected pair of said plurality of detected hydrocarbon gases, determining the ratio of the lighter to the heavier of said measured volumes of said preselected pair of hydrocarbon gases, and determining the quantitative measure of hydrocarbon reserves present in said selected linear incremental unit of subsurface earth formation functionally related to the values of said percentage of hydrocarbon gas saturation and a preselected range of said ratio of the lighter to the heavier of said preselected pair of hydrocarbon gases.

2. The method as described in claim 1, wherein said final determining step comprises the steps of:

selecting a first predetermined numerical conversion value if said ratio of hydrocarbon gases is within a first preselected range of values, selecting a second predetermined numerical conversion value if said ratio of hydrocarbon gases is within a second preselected range of values, multiplying said percentage of gas saturation by either of said first or second predetermined numerical conversion values to determine the quantitative measure of hydrocarbon reserves present in the subsurface earth formation.

3. The method as described in claim 1, wherein said linear incremental units of depth are one-foot depth increments.

4. The method as described in claim 3, wherein said preselected unit volume of drilling fluid is expressed in barrels.

5. The method as described in claim 4, wherein said step of determining the percentage of hydrocarbon gas saturation is determined in accordance with the following equation:

$$\% \ GASAT = \frac{(\% \ Gas)(Bbl \ Mud)(5.6146)(14.65)(460 + BHT)}{(14.65 + BHP)(460 + 100)} \times \frac{1}{(.00545 \ D^2)}$$

$$\% \ GASAT = \frac{(\% \ Gas)(Bbl \ Mud)(5.6146)(14.65)(460 + BHT)}{(14.65 + BHP)(460 + 100)} \times \frac{1}{(.00545 \ D^2)}$$

where:

%  GASAT = volume of hydrocarbons present in a cylindrical subsurface formation volume having an incremental depth of one foot, expressed in percent;

%  GAS = volume of hydrocarbon gases per barrel of circulated drilling fluid at earth surface conditions, expressed in percent;

Bbl Mud = volume of drilling fluid circulated in the borehole per vertical borehole foot drilled;

BHT = bottomhole temperature in °F. at a selected borehole depth;

BHP = bottomhole pressure in psi at a selected borehole depth; and

D = drill bit diameter in inches.

6. The method as described in claim 5, wherein said detected plurality of preselected hydrocarbon gases may be those gases conventionally referred to as $C_1$, $C_2$, $C_3$ and $C_4$.

7. The method as described in claim 6, wherein said preselected pair of hydrocarbon gases comprise $C_1$ = methane and $c_2$ = ethane.

8. The method as described in claim 7, wherein said ratio of the lighter to the heavier of said pair of measured volumes of hydrocarbon gases is expressed as $C_1/C_2$.

9. The method as described in claim 2, wherein said first predetermined numerical conversion value is 7758.34 when said first preselected range of said ratio of hydrocarbon gases is $2 < C_1/C_2 < 6$.

10. The method as described in claim 2, wherein said second predetermined numerical conversion value is 43.56 when said second preselected range of said ratio of hydrocarbon gases is $6 < C_1/C_2 < 50$.

11. A method of direct quantitative determination of a measure of hydrocarbon reserves present in a subsurface earth formation, while drilling a borehole therethrough with a drill bit, comprising the steps of:

measuring the vertical depth of said borehole in feet, determining the volume of the subsurface earth formation displaced by the borehole per each foot of borehole depth, measuring the volume in barrels of drilling fluid circulated into the borehole during drilling per a selected one-foot increment of borehole depth, detecting the presence of hydrocarbon gases in a preselected unit volume of drilling fluid recovered at the earth's surface from said measured volume of drilling fluid, measuring the volume of said detected hydrocarbon gases present in said preselected unit volume of drilling fluid, determining the subsurface formation pressure and temperature associated with said selected one-foot increment of borehole depth, determining the percentage of hydrocarbon gas saturation for said selected one-foot increment of borehole depth in the subsurface earth formation that is functionally related to said volume of hydrocarbon gases recovered at the earth's surface per said preselected unit volume of drilling fluid expressed as a percentage of said volume of the subsurface earth formation displaced by the borehole in said selected one-foot increment of borehole depth, correcting said determined percentage of hydrocarbon gas saturation for the subsurface earth formation to the subsurface earth formation pressure and temperature at said selected one-foot increment of borehole depth, detecting the presence of a plurality of preselected hydrocarbon gases present in said preselected unit volume of drilling fluid recovered at the earth's surface from said measured volume of drilling fluid, measuring the volume of each of a preselected pair of said plurality of detected hydrocarbon gases, determining the ratio of the lighter to the heavier of said measured volumes of said preselected pair of hydrocarbon gases, selecting a first predetermined numerical conversion value if said ratio of hydrocarbon gases is within a first preselected range of values, selecting a second predetermined numerical conversion value if said ratio of hydrocarbon gases is within a second preselected range of values, determining the quantitative measure of hydrocarbon reserves present in the subsurface earth formation functionally related to the product of said corrected percentage of a gas saturation by either said first or second predetermined numerical conversion value dependent on which of said first and second preselected range of values that said ratio of hydrocarbon gases falls within.

12. The method as described in claim 11, wherein said step of determining the percentage of hydrocarbon gas saturation is determined in accordance with the following equation:

$$\% \, GASAT = \frac{(\% \, Gas)(Bbl \, Mud)(5.6146)(14.65)(460 + BHT)}{(14.65 + BHP)(460 + 100)} \times$$

$$\frac{1}{(.00545 \, D^2)}$$

where:

% GASAT = volume of hydrocarbons present in a cylindrical subsurface formation volume having an incremental depth of one foot, expressed in percent;

% GAS = volume of hydrocarbon gases per barrel of circulated drilling fluid at earth surface conditions, expressed in percent;

Bbl Mud = volume of drilling fluid circulated in the borehole per vertical borehole foot drilled;

BHT = bottomhole temperasture in °F. at a selected borehole depth;

BHP = bottomhole pressure in psi at a selected borehole depth; and

D = drill bit diameter in inches.

13. The method as described in claim 12, wherein said preselected pair of hydrocarbon gases comprise $C_1$ = methane and $C_2$ = ethane.

14. The method as described in claim 13, wherein said ratio of the lighter to the heavier of said pair of measured volumes of hydrocarbon gases is expressed as $C_1/C_2$.

15. The method as described in claim 11, wherein said first predetermined numerical conversion value is 7758.34 when said first preselected range of said ratio of hydrocarbon gases is equal to $2 < C_1/C_2 < 6$.

16. The method as described in claim 11, wherein said second predetermined numerical conversion value is 43.56 when said second preselected range of said ratio of hydrocarbon gases is equal to $6 < C_1/C_2 < 50$.

17. A system for determining a direct quantitative measure of hydrocarbon reserves present in a subsurface earth formation, while drilling a borehole therethrough with a drill bit, comprising:

means for measuring the vertical depth of said borehole in linear incremental units, means for determining the volume of the subsurface earth formation displaced by the borehole per each of said linear incremental units of depth, means for measuring the volume of drilling fluid circulated into the borehole during drilling per a selected linear incremental unit of depth, means for detecting the presence of hydrocarbon gases in a preselected unit volume of drilling fluid recovered at the earth's surface from said measured volume of drilling fluid, means for measuring the volume of said detected hydrocarbon gases present in said preselected unit volume of drilling fluid, means for determining the subsurface formation pressure and temperature associated with said selected linear incremental unit of borehole depth, associated with said preselected unit volume of drilling fluid carrying said hydrocarbon gases, a computer for determining the percentage of hydrocarbon gas saturation for said selected linear incremental unit of borehole depth in the subsurface earth formation that is functionally related to said volume of hydrocarbon gases recovered at the earth's surface present in said preselected unit volume of drilling fluid corrected to the subsurface earth formation pressure and temperature at said selected linear incremental unit of borehole depth expressed as a percentage of said volume of the subsurface earth formation displaced by the borehole in said selected linear incremental unit of borehole depth, means for detecting the presence of a plurality of preselected hydrocarbon gases present in said preselected unit volume of drilling fluid recovered at the earth's surface from said measure volume of drilling fluid, and means for measuring the volume of each of a preselected pair of said plurality of detected hydrocarbon gases, wherein said computer determines the ratio of the lighter to the heavier of said measured volumes of said preselected pair of hydrocarbon gases, and wherein said computer determines the quantitative measure of hydrocarbon reserves present in said selected linear incremental unit of subsurface earth formation functionally related to the values of said percentage of hydrocarbon gas saturation and a preselected range of said ratio of the lighter to the heavier of said preselected pair of hydrocarbon gases.

18. The system as described in claim 17, wherein said computer selects a first predetermined numerical conversion value if said ratio of hydrocarbon gases is within a first preselected range of values, wherein said computer selects a second predetermined numerical conversion value if said ratio of hydrocarbon gases is within a second preselected range of values, and wherein said computer multiplies said percentage of gas saturation by either said first or second predetermined numerical conversion value to determine the quantitative measure of hydrocarbon reserves present in the subsurface earth formation.

19. The system as described in claim 17, wherein said linear incremental units of depth are one-foot depth increments.

20. The system as described in claim 19, wherein said preselected unit volume of drilling fluid is expressed in barrels.

21. The system as described in claim 20, wherein said computer determines the percentage of hydrocarbon gas saturation in accordance with the following equation:

$$\% \ GASAT = \frac{(\% \ Gas)(Bbl \ Mud)(5.6146)(14.65)(460 + BHT)}{(14.65 + BHP)(460 + 100)} \times \frac{1}{(.00545 \ D^2)}$$

where:
- $\% \ GASAT$ = volume of hydrocarbons present in a cylindrial subsurface formation volume having an incremental depth of one foot, expressed in percent;
- $\% \ GAS$ = volume of hydrocarbon gases per barrel of circulated drilling fluid at earth surface conditions, expressed in percent;
- $Bbl \ Mud$ = volume of drilling fluid circulated in the borehole per vertical borehole foot drilled;
- $BHT$ = bottomhole temperature in °F. at a selected borehole depth;
- $BHP$ = bottomhole pressure in psi at a selected borehole depth; and
- $D$ = drill bit diameter in inches.

22. The system as described in claim 21, wherein said detected plurality of preselected hydrocarbon gases may be those gases conventionally referred to as $C_1$, $C_2$, $C_3$ and $C_4$.

23. The system as described in claim 22, wherein said preselected pair of hydrocarbon gases comprise $C_1$ = methane and $C_2$ = ethane.

24. The system as described in claim 23, wherein said ratio of the lighter to the heavier of said pair of measured volumes of hydrocarbon gases is expressed as $C_1/C_2$.

25. The system as described in claim 24, wherein said first predetermined numerical conversion value is 7758.34 when said first preselected range of said ratio of hydrocarbon gases is $2 < C_1/C_2 < 6$.

26. The system as described in claim 24, wherein said second predetermined numerical conversion value is 43.56 when said second preselected range of said ratio of hydrocarbon gases is $6 < C_1/C_2 < 50$.

* * * * *